United States Patent
Higuchi et al.

(10) Patent No.: US 9,850,386 B2
(45) Date of Patent: Dec. 26, 2017

(54) PHOTO-CURABLE COATING COMPOSITION AND COATED ARTICLE

(71) Applicant: Shin-Etsu Chemical Co., Ltd., Tokyo (JP)

(72) Inventors: Koichi Higuchi, Annaka (JP); Yukimasa Aoki, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 164 days.

(21) Appl. No.: 14/746,359

(22) Filed: Jun. 22, 2015

(65) Prior Publication Data

US 2015/0368474 A1 Dec. 24, 2015

(30) Foreign Application Priority Data

Jun. 23, 2014 (JP) ................. 2014-128136

(51) Int. Cl.

| | |
|---|---|
| *C08F 220/26* | (2006.01) |
| *C08F 220/36* | (2006.01) |
| *C08K 9/06* | (2006.01) |
| *C09D 5/32* | (2006.01) |
| *C09D 7/12* | (2006.01) |
| *C09D 133/04* | (2006.01) |
| *C07D 251/24* | (2006.01) |
| *C09D 4/00* | (2006.01) |
| *C09D 5/00* | (2006.01) |
| *C08F 222/10* | (2006.01) |
| *C08K 5/00* | (2006.01) |
| *C08K 5/3492* | (2006.01) |
| *C09D 133/06* | (2006.01) |

(52) U.S. Cl.
CPC .............. *C09D 4/00* (2013.01); *C08F 222/10* (2013.01); *C08K 5/00* (2013.01); *C09D 5/00* (2013.01); *C09D 7/1225* (2013.01); *C09D 7/1241* (2013.01); *C09D 133/06* (2013.01); *C07D 251/24* (2013.01); *C08F 220/26* (2013.01); *C08F 220/36* (2013.01); *C08K 5/3492* (2013.01); *C08K 9/06* (2013.01); *C09D 5/32* (2013.01); *C09D 133/066* (2013.01); *Y10T 428/259* (2015.01); *Y10T 428/31906* (2015.04); *Y10T 428/31935* (2015.04)

(58) Field of Classification Search
CPC .................................................. C07D 251/24
See application file for complete search history.

(56) References Cited

U.S. PATENT DOCUMENTS

| | | |
|---|---|---|
| 4,390,660 A | 6/1983 | Ashby |
| 4,555,559 A | 11/1985 | Kimura et al. |
| 5,391,795 A | 2/1995 | Pickett |
| 5,990,188 A | 11/1999 | Patel et al. |
| 9,670,167 B2 * | 6/2017 | Higuchi .............. C07D 251/24 |
| 2007/0238804 A1 * | 10/2007 | Ho ...................... A61K 6/0017 522/77 |
| 2011/0151218 A1 | 6/2011 | Meyer Zu Berstenhorst et al. |
| 2012/0059080 A1 | 3/2012 | Fukushima et al. |
| 2012/0094127 A1 | 4/2012 | Meyer Zu Berstenhorst et al. |
| 2012/0243115 A1 | 9/2012 | Takamiya et al. |
| 2016/0017169 A1 * | 1/2016 | Kostromine .......... C09D 175/14 428/412 |

FOREIGN PATENT DOCUMENTS

| | | |
|---|---|---|
| EP | 0 668 313 A1 | 8/1995 |
| EP | 0 824 119 A2 | 2/1998 |
| EP | 2 427 440 A1 | 3/2012 |
| EP | 2 786 987 A1 | 10/2014 |
| JP | 3-62177 B2 | 9/1991 |
| JP | 6-88065 A | 3/1994 |
| JP | 6-88066 A | 3/1994 |
| JP | 7-278525 A | 10/1995 |
| JP | 2010-270230 A | 12/2010 |
| JP | 4750914 B2 | 8/2011 |
| JP | 2012-31434 A | 2/2012 |
| JP | 2012-167288 A | 9/2012 |
| JP | 2012 526159 A | 10/2012 |
| JP | 2012-219102 A | 11/2012 |
| JP | 2014-058179 A | 4/2014 |
| WO | WO 2010/127805 A1 | 11/2010 |

OTHER PUBLICATIONS

Extended European Search Report dated Oct. 5, 2015, in European Patent Application No. 15172199.0.

* cited by examiner

*Primary Examiner* — Ramsey Zacharia

(74) *Attorney, Agent, or Firm* — Birch, Stewart, Kolasch & Birch, LLP

(57) ABSTRACT

A photo-curable coating composition comprising (1) a polyfunctional (meth)acrylic monomer, (2) a photopolymerization initiator, and (3) a specific hydroxyphenyltriazine base UV absorber has high mar resistance and long-term weather resistance.

7 Claims, No Drawings

PHOTO-CURABLE COATING COMPOSITION AND COATED ARTICLE

CROSS-REFERENCE TO RELATED APPLICATION

This non-provisional application claims priority under 35 U.S.C. §119(a) on Patent Application No. 2014-128136 filed in Japan on Jun. 23, 2014, the entire contents of which are hereby incorporated by reference.

TECHNICAL FIELD

This invention relates to a novel photo-curable coating composition and a coated article.

BACKGROUND ART

Thermoplastic substrates such as polycarbonates and poly(methyl methacrylate) are generally characterized by their many advantageous properties such as clarity, high ductility, high heat deflection temperature as well as dimensional stability. Many of these materials are transparent and are conventionally employed as replacements for glass in many commercial applications. However, such materials easily scratch and abrade, resulting in possible decrease in transparency. They are also susceptible to degradation by ultraviolet (UV) light, giving rise to problems like yellowing and whitening of the substrate surface. One solution to such problems is by applying a mar resistant coating composition containing a UV absorber onto the surface of resin substrates.

However, the mar resistant coating films containing a UV absorber have the drawbacks that the UV absorber can bleed out or flow away, failing to exert its desired properties, and the addition of the UV absorber detracts from essential mar resistance performance. In one approach to address these drawbacks, a UV absorber is attached and anchored to a binder component in the mar resistant coating film to prevent the film from losing weather resistance and mar resistance due to bleed-out and outflow. To this end, the UV absorber must be designed in compliance with the main chain structure and crosslinking mode of the binder.

For example, silicone hardcoat compositions cure into hardcoat films with good mar resistance and durability via crosslinking reaction involving silanol (SiOH) condensation of a precursor in the form of a hydrolytic condensate of an alkoxysilane. Of the UV absorbers used in such silicone hardcoat compositions, UV absorbers having introduced reactive groups for silanol crosslinking are known from Patent Documents 1 to 4. However, the process for preparing the reactive silyl-modified UV absorber has some problems including a multi-stage synthetic route and removal of a hydrosilylation catalyst. Generally, no tight adhesion to a resin substrate is achievable unless a silicone hardcoat film is laid on the substrate via a primer layer. This necessitates an extra process including preparation, coating and curing of the primer.

Another known mar resistant coating is a photo-curable (meth)acrylic coating composition. The photo-curable (meth)acrylic coating composition comprises at least one polyfunctional (meth)acrylate and a photopolymerization initiator. Crosslinking takes place via photopolymerization of (meth)acrylic groups on the polyfunctional (meth)acrylate, forming a film. Reactive group-introduced UV absorbers are added to such photo-curable (meth)acrylic coating compositions as reported in Patent Documents 5 to 9. The photo-curable (meth)acrylic coating composition comprising the reactive group-introduced UV absorber can be directly applied and cured to a resin substrate without a need for primers which are required in the above-mentioned silicone hardcoat compositions. However, there still remain some outstanding issues.

Patent Documents 5 and 6 disclose alkoxysilyl-bearing dibenzoyl resorcinol derivatives as another example of the reactive group-introduced UV absorber. Since the alkoxysilyl group in this UV absorber is not involved in crosslinking reaction of the photo-curable (meth)acrylic coating, the cured film is estimated short in mar resistance. In fact, these documents do not refer to mar resistance. With respect to long-term weather resistance, there is a possibility of the UV absorber bleeding out because the UV absorber has not been reacted with the binder.

Patent Documents 7 and 8 describe silsesquioxanes having a (meth)acrylic functional benzotriazole as a UV absorbing group. Although the solubility of the UV absorber in a polyfunctional (meth)acrylate is improved over the unmodified benzotriazole base UV absorbers, it is still insufficient for high loadings. This UV absorber has a relatively large moiety such as silsesquioxane skeleton which does not contribute to UV absorption. That is, this UV absorber has a low UV absorbing group content, provided that the "UV absorbing group content" is defined as a proportion of UV absorbing groups per molecular weight of the absorber. Inevitably the UV absorber must be added in a large amount in order to obtain a necessary UV absorbing capacity, which tends to detract from the desired properties (e.g., mar resistance and adhesion) except weather resistance.

Patent Document 9 discloses a photo-curable (meth)acrylic polymer having both a UV absorbing group and a (meth)acryloyl group as side chains. The (meth)acrylic polymer reacts with a polyfunctional (meth)acrylate in the photo-curable (meth)acrylic coating composition whereby it is anchored in the film. The UV absorber also has improved solubility in the polyfunctional (meth)acrylate, but a low UV absorbing group content because of the polymer form. The UV absorber must be added in a large amount, which tends to detract from mar resistance and adhesion.

Also known are (meth)acrylic functional UV absorbers having a high UV absorbing group content and a relatively low molecular weight. Typical of commercially available absorbers is 2-[2'-hydroxy-5'-(methacryloyloxyethyl)phenyl]-2H-benzotriazole (trade name RUVA-93 from Otsuka Chemical Co., Ltd.).

Patent Documents 10 and 11 disclose benzotriazole and benzophenone base UV absorbers in which an unsaturated double bond is attached to a urethane bond via an alkylene chain, respectively. It is generally known that benzophenone and resorcinol base UV absorbers exhibit insufficient UV absorbing capacity while some benzotriazole base UV absorbers are toxic. Those benzotriazole base UV absorbers which are safe have a low solubility, with their amount of addition being limited.

In connection with a photo-curable (meth)acrylic coating composition which can be applied directly on a resin substrate without a need for primers, it is desired to have a UV absorber which is fully soluble in a polyfunctional (meth)acrylate, has a high UV absorbing group content, and does not compromise the mar resistance and adhesion of a coating film.

CITATION LIST

Patent Document 1: JP-B H03-14862 (U.S. Pat. No. 4,390,660)

Patent Document 2: JP-B H03-62177 (U.S. Pat. No. 4,555, 559)
Patent Document 3: JP-A H07-278525 (U.S. Pat. No. 5,391, 795, EP 0668313)
Patent Document 4: JP-A 2012-526159 (US 2012094127, EP 2427440)
Patent Document 5: JP 4750914 (U.S. Pat. No. 5,990,188, EP 0824119)
Patent Document 6: JP-A 2012-167288 (U.S. Pat. No. 5,990,188, EP 0824119)
Patent Document 7: JP-A 2010-270230
Patent Document 8: JP-A 2012-219102
Patent Document 9: JP-A 2012-031434
Patent Document 10: JP-A H06-88065
Patent Document 11: JP-A H06-88066

DISCLOSURE OF INVENTION

An object of the invention is to provide a coating composition comprising a (meth)acrylic group-bearing benzotriazine base UV absorber having a high UV absorbing capacity and solubility in a polyfunctional (meth)acrylate, which cures into a coating film having mar resistance and adhesion and capable of retaining the UV absorber therein stably without bleed-out, and a coated article having a cured film thereof.

In one aspect, the invention provides a photo-curable coating composition comprising (1) a polyfunctional (meth)acrylic monomer, (2) a photopolymerization initiator, and (3) a hydroxyphenyltriazine base UV absorber having the general formula (1).

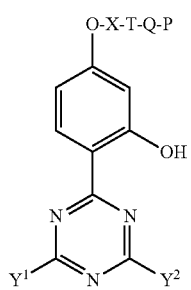

(1)

Herein $Y^1$ and $Y^2$ are each independently a substituent having the general formula (2):

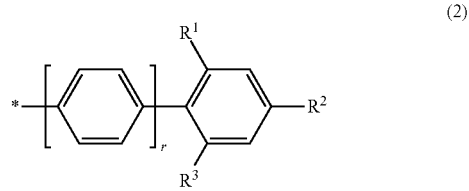

(2)

wherein * designates a bonding site, r is 0 or 1, $R^1$, $R^2$ and $R^3$ are each independently hydrogen, or hydroxyl, C1-C20 alkyl, C4-C12 cycloalkyl, C2-C20 alkenyl, C1-C20 alkoxy, C4-C12 cycloalkoxy, C2-C20 alkenyloxy, C7-C20 aralkyl, halogen, —C≡N, C1-C5 haloalkyl, —SO$_2$R', —SO$_3$H, —SO$_3$M wherein M is an alkali metal, —COOR', —CONHR', —CONR'R", —OCOOR', —OCOR', —OCONHR', (meth)acrylamino, (meth)acryloxy group, optionally substituted C6-C12 aryl or optionally substituted C3-C12 heteroaryl group, wherein R' and R" are independently hydrogen, C1-C20 alkyl, C4-C12 cycloalkyl, optionally substituted C6-C12 aryl or optionally substituted C3-C12 heteroaryl group; X is a divalent, straight or branched, saturated hydrocarbon residue which may be separated by at least one atom selected from oxygen, nitrogen, sulfur, and phosphorus; T is a urethane group: —O—(C═O)—NH—; Q is a divalent, straight or branched, saturated hydrocarbon residue which may be separated by at least one atom selected from oxygen, nitrogen, sulfur, and phosphorus; and P is a (meth)acryloxy group.

In a preferred embodiment, X has the general formula (3) or (4):

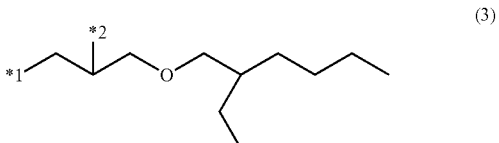

(3)

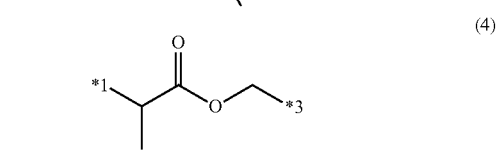

(4)

wherein *1 bonds to oxygen in formula (1), *2 bonds to T in formula (1), and *3 bonds to T in formula (1) directly or through a divalent, straight or branched, saturated hydrocarbon group which may be separated by at least one atom selected from oxygen, nitrogen, sulfur, and phosphorus. Q has the general formula (5):

(5)

wherein *4 bonds to T in formula (1) and *5 bonds to P in formula (1).

In a preferred embodiment, $R^1$, $R^2$ and $R^3$ in formula (1) are each independently hydrogen or methyl, X is formula (3), and Q is formula (5).

In a preferred embodiment, the polyfunctional (meth)acrylic monomer is at least one monomer selected from the group consisting of dipentaerythritol penta(meth)acrylate, dipentaerythritol hexa(meth)acrylate, tris(2-(meth)acryloxyalkyl)isocyanurate, polyurethane poly(meth)acrylate having at least 5 (meth)acrylic groups in the molecule, and polyester poly(meth)acrylate having at least 5 (meth)acrylic groups in the molecule.

Preferably, the composition may further comprise colloidal silica which is surface treated with a (meth)acrylic functional alkoxysilane.

Preferably, the composition may further comprise at least one member selected from among hindered amine photostabilizers, metal oxide fine particles other than the alkoxysilane-surface-treated colloidal silica defined above, and UV absorbers other than formula (1).

In another aspect, the invention provides a coated article comprising a substrate and a cured film of the photo-curable coating composition defined herein formed on the substrate directly or via another layer or layers. Typically, the substrate is an organic resin or wood.

Advantageous Effects of Invention

The photo-curable coating composition of the invention can retain a UV absorber in its coating film stably without bleed-out. It exhibits a high level of mar resistance and long-term weather resistance.

DESCRIPTION OF PREFERRED EMBODIMENTS

The notation (Cn-Cm) means a group containing from n to m carbon atoms per group. As employed herein, the terminology "(meth)acrylic" is intended to mean "acrylic or methacrylic". "Optional" or "optionally" means that the subsequently described event or circumstances may or may not occur, and that description includes instances where the event or circumstance occurs and instances where it does not.

(1) Polyfunctional (Meth)Acrylic Monomer

Component (1) is a monomer which is not particularly limited as long as it has a plurality of (meth)acrylic groups in the molecule and is photo-curable. Examples of the monomer which can be used herein include polyfunctional (meth)acrylates having a polymerizable unsaturated bond such as polyfunctional (meth)acrylate, urethane (meth)acrylate, epoxy (meth)acrylate, and polyester (meth)acrylate. A suitable monomer may be selected based on the desired coating properties.

Examples of the polyfunctional (meth)acrylate include hexanediol di(meth)acrylate, octanediol di(meth)acrylate, decanediol di(meth)acrylate, neopentyl glycol di(meth)acrylate, ethylene glycol di(meth)acrylate, polyethylene glycol (repeating unit number (referred to as "n" hereinafter)=2 to 15) di(meth)acrylate, polypropylene glycol (n=2 to 15) di(meth)acrylate, polybutylene glycol (n=2 to 15) di(meth)acrylate, 2,2-bis(4-(meth)acryloxyethoxyphenyl)propane, 2,2-bis(4-(meth)acryloxydiethoxyphenyl)propane, trimethylolpropane diacrylate, bis(2-(meth)acryloxyethyl)hydroxyethyl isocyanurate, trimethylolpropane tri(meth)acrylate, tris(2-(meth)acryloxyethyl)isocyanurate, pentaerythritol tri(meth)acrylate, pentaerythritol tetra(meth)acrylate, dipentaerythritol tetra(meth)acrylate, dipentaerythritol penta(meth)acrylate, dipentaerythritol hexa(meth)acrylate, epoxy poly(meth)acrylates such as epoxy di(meth)acrylate which is obtained by reaction of bisphenol A diepoxy with (meth) acrylic acid, urethane tri(meth)acrylate which is obtained by reaction of a trimer of 1,6-hexamethylene diisocyanate with 2-hydroxyethyl (meth)acrylate, urethane di(meth)acrylate which is obtained by reaction of isophorone diisocyanate with 2-hydroxypropyl (meth) acrylate, urethane hexa(meth) acrylate which is obtained by reaction of isophorone diisocyanate with pentaerythritol tri(meth)acrylate, urethane di(meth)acrylate which is obtained by reaction of dicyclomethane diisocyanate with 2-hydroxyethyl (meth) acrylate, urethane poly(meth)acrylates such as urethane di(meth) acrylate which is obtained by reaction of a urethanated reaction product between dicyclomethane diisocyanate and poly(n=6 to 15) tetramethylene glycol with 2-hydroxyethyl (meth)acrylate, polyester poly(meth)acrylates such as polyester (meth)acrylate which is obtained by reaction of trimethylolethane, succinic acid and (meth)acrylic acid, and polyester (meth)acrylate which is obtained by reaction of trimethylolpropane, succinic acid, ethylene glycol and (meth)acrylic acid.

Of these, dipentaerythritol penta(meth)acrylate, dipentaerythritol hexa(meth)acrylate, tris(2-(meth)acryloxyethyl) isocyanurate, polyurethane poly(meth)acrylates having at least 5 radically polymerizable unsaturated double bonds such as (meth)acrylic groups in the molecule, and polyester poly(meth)acrylates having at least 5 radically polymerizable unsaturated double bonds such as (meth)acrylic groups in the molecule are preferred.

If necessary, component (1) may be a combination of two or more monomers. Particularly, a combination of one or two types of polyfunctional (meth)acrylate and polyurethane poly(meth)acrylate offers the advantages that the composition forms a coating having improved heat resistance, chemical resistance, durability, and adhesion to substrate.

(2) Photopolymerization Initiator

Component (2) is a photopolymerization initiator which is not particularly limited and may be suitably selected based on compatibility and curability in the photo-curable coating composition.

Examples of component (2) include carbonyl compounds such as benzoin, benzoin monomethyl ether, benzoin isopropyl ether, acetoin, benzil, benzophenone, p-methoxybenzophenone, diethoxyacetophenone, benzyl dimethyl ketal, 2,2-diethoxyacetophenone, 1-hydroxycyclohexyl phenyl ketone, methyl phenylglyoxylate, 2-hydroxy-2-methyl-1-phenylpropan-1-one; sulfur compounds such as tetramethylthiuram monosulfide and tetramethylthiuram disulfide; phosphorus compounds such as 2,4,6-trimethylbenzoyl diphenylphosphine oxide, 2,4,6-trimethylbenzoyl phenyl ethoxyphosphine oxide, bis(2,4,6-trimethylbenzoyl)phenylphosphine oxide, bis(2,6-dimethoxybenzoyl)-2,4,4-trimethylpentylphosphine oxide; 2-benzyl-2-dimethylamino-1-(4-morpholinophenyl)-butanone-1, and camphorquinone. Of these, 2,4,6-trimethylbenzoyl diphenylphosphine oxide, 2,4,6-trimethylbenzoyl phenyl ethoxyphosphine oxide, bis(2,4,6-trimethylbenzoyl)phenylphosphine oxide, and bis(2,6-dimethoxybenzoyl)-2,4,4-trimethylpentylphosphine oxide are preferred. These compounds may be used alone or in admixture of two or more while they may be combined in any ratio depending on the desired coating properties.

The content of component (2) is preferably 0.1 to 10 parts by weight, more preferably 1 to 8 parts by weight per 100 parts by weight of components (1) and (3) combined. If the content of component (2) is less than 0.1 part by weight, the coating may have a significantly slow cure rate and become poor in mar resistance and substrate adhesion. If the content of component (2) is more than 10 parts by weight, the cured coating may be colored or have poor weather resistance.

(3) (Meth)Acrylic Group-Bearing Hydroxyphenyltriazine Base UV Absorber

Component (3) is a hydroxytriazine base UV absorber having formula (1).

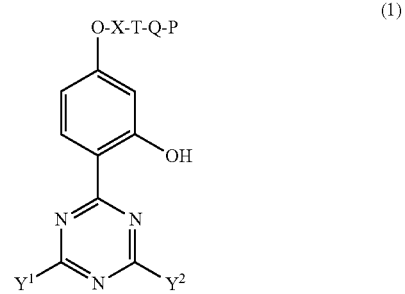

(1)

Herein $Y^1$ and $Y^2$ are each independently a substituent having the general formula (2).

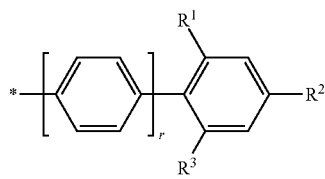
(2)

Herein * designates a bonding site, r is 0 or 1, preferably 1. In case of r=1, the compound is stabilized due to expansion of the conjugated system of radicals generated on UV absorption.

$R^1$, $R^2$ and $R^3$ are each independently hydrogen, or hydroxyl, C1-C20 alkyl, C4-C12 cycloalkyl, C2-C20 alkenyl, C1-C20 alkoxy, C4-C12 cycloalkoxy, C2-C20 alkenyloxy, C7-C20 aralkyl, halogen, —C≡N, C1-C5 haloalkyl, —SO$_2$R', —SO$_3$H, —SO$_3$M wherein M is an alkali metal, —COOR', —CONHR', —CONR'R", —OCOOR', —OCOR', —OCONHR', (meth)acrylamino, (meth)acryloxy, optionally substituted (typically halo-substituted) C6-C12 aryl or optionally substituted (typically halo-substituted) C3-C12 heteroaryl. Of these, hydrogen, hydroxyl, C1-C20 alkyl, C1-C20 alkoxy, halogen, and C6-C12 aryl are preferred, with hydrogen and C1-C20 alkyl being more preferred.

R' and R" are independently hydrogen, C1-C20 alkyl, C4-C12 cycloalkyl, optionally substituted (typically halo-substituted) C6-C12 aryl or optionally substituted (typically halo-substituted) C3-C12 heteroaryl. Of these, hydrogen, C1-C20 alkyl, and C6-C12 aryl are preferred, with hydrogen and C1-C20 alkyl being more preferred.

X is a divalent, straight or branched, saturated hydrocarbon residue, such as C1-C20 alkylene or C4-C12 cycloalkylene, which may be separated by at least one atom of oxygen, nitrogen, sulfur, and phosphorus. Of these, groups having the general formulae (3) and (4) are preferred for ease of synthesis and availability of the reactants.

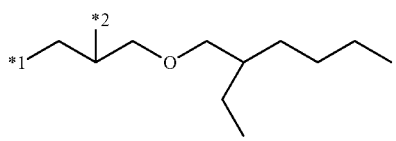
(3)

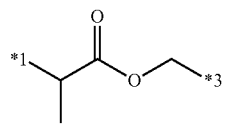
(4)

Herein *1 bonds to oxygen in formula (1), *2 bonds to T in formula (1), and *3 bonds to T in formula (1) directly or through a divalent, straight or branched, saturated hydrocarbon group which may be separated by at least one atom of oxygen, nitrogen, sulfur, and phosphorus.

T is a urethane group: —O—(C=O)—NH—.

Q is a divalent, straight or branched, saturated hydrocarbon residue, such as C1-C20 alkylene or C4-C12 cycloalkylene, which may be separated by at least one atom of oxygen, nitrogen, sulfur, and phosphorus. Of these, a group having the general formula (5) is preferred for ease of synthesis and availability of the reactants.

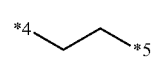
(5)

Herein *4 bonds to T in formula (1), and *5 bonds to P in formula (1).

P is a (meth)acryloxy group, specifically having the general formula (6):

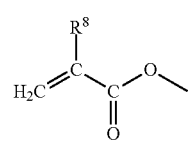
(6)

wherein $R^8$ is hydrogen or methyl.

Examples of component (3) include the following compounds, which are preferred because of ease of synthesis, compatibility with a polyfunctional (meth)acrylate and the like, photo-curability.

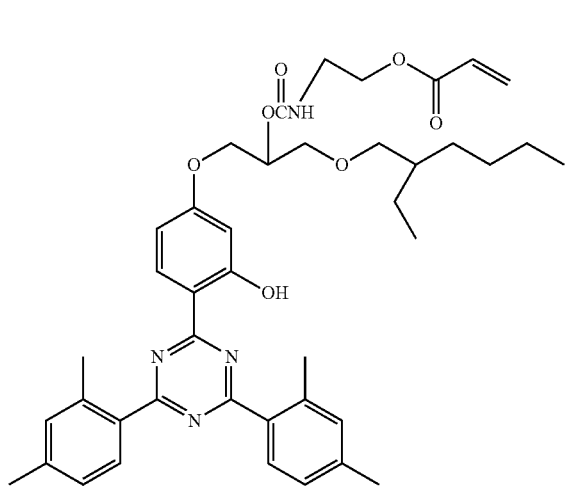
(7)

(8)

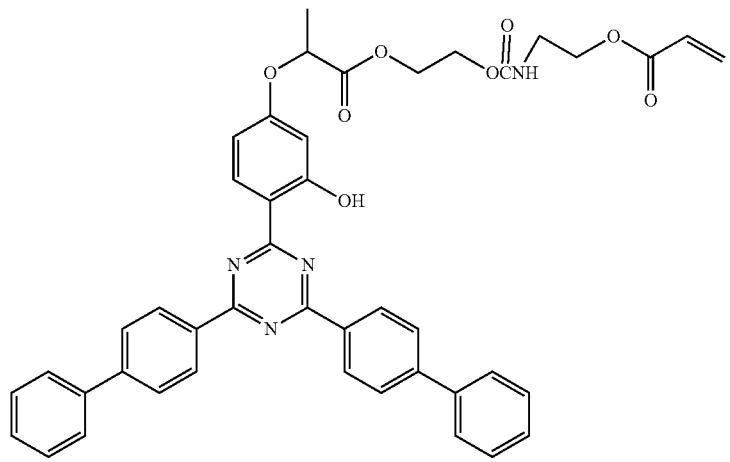

(9)

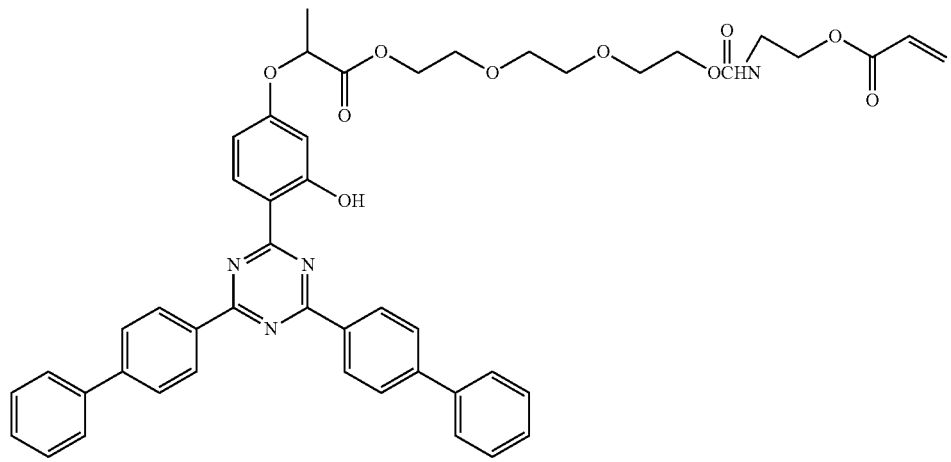

(10)

Component (3) may be prepared by the method described in Japanese Patent Application No. 2014-058179.

In the photo-curable coating composition, a hydrolyzate/condensate of (meth)acryloyloxyalkoxysilane or an organic-inorganic hybrid (meth)acrylate which is obtained by hydrolytic condensation between colloidal silica and (meth)acryloyloxyalkoxysilane may be added, if necessary, for the purpose of improving the hardness and durability of the coating. Examples include organic-inorganic hybrid vinyl compounds and organic-inorganic hybrid (meth)acrylic compounds, which are obtained by (co)hydrolytic condensation of a single silane or a mixture of silanes, such as, for example, vinyltrimethoxysilane, vinyltriethoxysilane, p-styryltrimethoxysilane, 3-(meth)acryloxypropylmethyldimethoxysilane, 3-(meth)acryloxypropyltrimethoxysilane, 2-(meth)acryloxyethyltrimethoxysilane, 2-(meth)acryloxyethyltriethoxysilane, (meth) acryloxymethyltrimethoxysilane, (meth) acryloxymethyltriethoxysilane, 3-(meth)acryloxypropylmethyldiethoxysilane, 3-(meth)acryloxypropyltriethoxysilane, 8-(meth)acryloxyoctyltrimethoxysilane, and 8-(meth)acryloxyoctyltriethoxysilane, optionally in the presence of colloidal silica. Of these, colloidal silica surface treated with 3-(meth)acryloxypropyltrimethoxysilane, which falls in the concept of organic-inorganic hybrid (meth)acrylate, is preferred from the aspects of ease of radical polymerization and mar resistance.

The photo-curable coating composition may optionally contain various additives such as UV absorbers other than component (3), organic solvents, antifouling agents, water repellents, leveling agents, colorants, pigments, antioxidants, yellowing inhibitors, bluing agents, defoamers, thickeners, anti-settling agents, antistatic agents, surfactants, adhesion promoters, IR absorbers, photostabilizers, curing catalysts, and metal oxide fine particles. Especially, the photo-curable coating composition may further comprise at least one additive selected from among antifouling agents, water repellents, leveling agents, colorants, pigments, adhesion promoters, IR absorbers, photostabilizers, curing catalysts other than the polymerization initiator described above, metal oxide fine particles other than the colloidal silica surface treated with a (meth)acrylic functional alkoxysilane, and UV absorbers other than component (3). Inter alia, at least one additive selected from the group consisting of hindered amine photostabilizers, metal oxide fine particles other than the alkoxysilane-surface-treated colloidal silica, and UV absorbers other than component (3) is more preferred.

The organic solvent is preferably selected in accordance with a particular coating method. Suitable solvents include alcoholic solvents such as isobutanol, glycol solvents such as propylene glycol monomethyl ether, ester solvents such as n-butyl acetate, ketone solvents such as methyl isobutyl ketone, and aromatic solvents such as toluene. These solvents are used alone or in an arbitrary combination such that the coating composition may have a viscosity of up to 20 mPa·s when it is applied by spray coating. Desirably, the coating composition has a viscosity of up to 100 mPa·s when it is applied by shower flow coating or dip coating. When the coating composition is a high solid type coating composition containing more than 80% by weight of solids, the solvent is selected in consideration of the solubilities of additives.

The thickness of a coating or film is not particularly limited although it is preferably 0.1 to 50 μm. A thickness of 1 to 30 μm is especially preferred for the hardness, mar resistance, long-term stable adhesion and crack resistance of the coating. A coating of thinner than 0.1 μm may be susceptible to cissing and have an insufficient UV absorbing capacity whereas a coating of thicker than 50 μm may be prone to crack.

The substrate used herein is not particularly limited and includes organic resin such as molded plastics, wood items, fibers, ceramics, glass, metals, and composites thereof. Of these, plastic materials are preferred. Examples include polycarbonate resins, polystyrene resins, acrylic resins, modified acrylic resins, urethane resins, thiourethane resins, polycondensates of halogenated bisphenol A and ethylene glycol, acrylic urethane resins, halogenated aryl-containing acrylic resins, sulfur-containing resins, polyalkylene terephthalate resins, cellulos resins, amorphous polyolefin resins, and composite resins thereof. These resin substrates which have been surface treated, specifically by chemical conversion treatment, corona discharge treatment, flame treatment, plasma treatment, acid or alkaline treatment are also useful. Also included are laminated substrates comprising a resin substrate and a surface layer formed thereon from a resin of different type from the substrate. Exemplary laminated substrates include those consisting of a polycarbonate resin substrate and a surface layer of acrylic resin or urethane resin and those consisting of a polyester resin substrate and a surface layer of acrylic resin, which are prepared by co-extrusion or lamination technique.

The coating composition may be applied to the surface of a substrate directly or via another layer or layers such as a primer layer, DV absorbing layer, printing layer, recording layer, heat-ray shielding layer, tacky layer, inorganic vapor-deposited layer and the like.

On the surface of a cured film of the photo-curable coating composition, another coating layer may optionally be formed, such as an adhesive layer, DV absorbing layer, printing layer, recording layer, heat-ray shielding layer, tacky layer, inorganic vapor-deposited layer, water/oil repellent layer and hydrophilic antifouling layer.

A coated article having a cured film of the photo-curable coating composition exhibits excellent mar resistance, UV absorbing capacity, heat resistance, water resistance, and bleed-out resistance.

The photo-curable coating composition is applied to a substrate, optionally air dried or heated for volatilizing off the solvent if any, and cured by light exposure. Examples of effective radiation include electron beams and ultraviolet rays emitted from high-pressure mercury lamps, metal halide lamps, LED lamps, and the like. The exposure may be done either in air or in an inert gas atmosphere such as nitrogen or argon.

Polycarbonates coated with the photo-curable coating composition have the advantage that the coating prevents surface yellowing and degradation of the polycarbonate and the coated polycarbonate has a surface hardness comparable to glass, and is lightweight and easy to mold. Thus the coated polycarbonates can be used in various applications such as headlamp lenses of automobiles, sensors and windows of vehicles, outdoor signboards, windows of greenhouses or outdoor buildings, roofs of terraces or garages, balconies, and covers of meters and gauges.

EXAMPLE

Examples are given below by way of illustration and not by way of limitation. All parts and % are by weight unless otherwise stated. The number average molecular weight (Mn) is determined by gel permeation chromatography (GPC) versus polystyrene standards.

GPC Analysis Conditions
Analyzer: HLC-8320GPC (Tosoh Co., Ltd.)
Column: TSKgel G4000HXL+G3000HXL+G2000HXL+ G2000HXL (Tosoh Co., Ltd.), all 6 mm ID×150 mm L
Developing solvent: tetrahydrofuran
Column oven temperature: 40° C.
Flow rate: 1 mL/min
Detector: refraction index (RI) detector
Standards: monodisperse polystyrene

[Synthesis of (Meth)Acrylic Group-Bearing Hydroxyphenyltriazine Base UV Absorber]

Synthesis Example 1

A 500-mL flask was charged with 29.2 g of 2-[4-[(2-hydroxy-3-(2'-ethyl)hexyl)oxy]-2-hydroxyphenyl]-4,6-bis (2,4-dimethylphenyl)-1,3,5-triazine (Tinuvin 405, BASF), 130 g of propylene glycol monomethyl ether acetate, and 0.04 g of methoxyphenol. The contents were stirred and heated at 80° C. in a 4% oxygen/nitrogen atmosphere. Then, 7.1 g of 2-acryloyloxyethyl isocyanate (Karenz AOI, Showa Denko K.K.) and 0.04 g of dioctyltin oxide were added to the mixture, after which the reaction was run at 80° C. for 5 hours. The reaction mixture was cooled to room temperature and passed through a silica gel-packed column. The eluate was concentrated under reduced pressure, yielding 32.8 g of compound (S1) having formula (7).

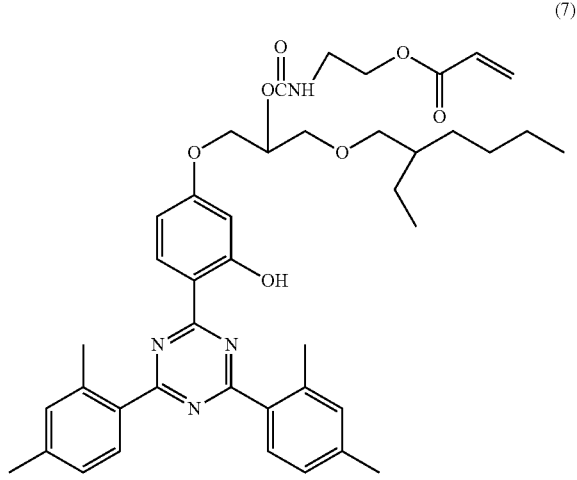

(7)

Synthesis Example 2

A 1-L flask was charged with 101.7 g of 2-[2-hydroxy-4-(1-octyloxycarbonylethoxyl)phenyl]-4,6-bis(4-phenylphenyl)-1,3,5-triazine (Tinuvin 479, BASF), 150 g of ethylene glycol, and 6 g of dioctyltin oxide. The contents were stirred and heated at 160° C. for 5 hours in a nitrogen atmosphere. The reaction mixture was cooled to room temperature and precipitated from methanol. The crystal was filtered and washed with methanol. Recrystallization from toluene gave a precursor having formula (11).

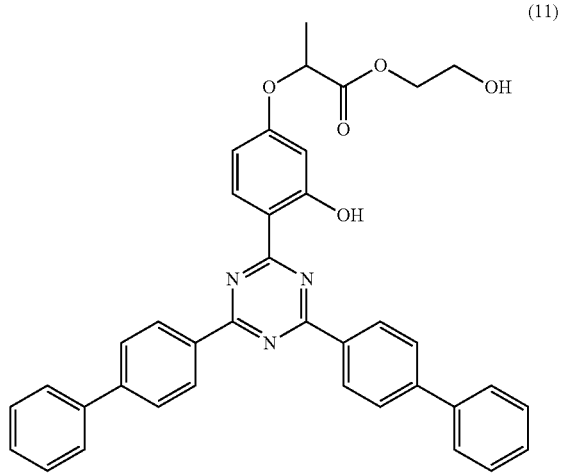 [SMILES: CC(Oc1ccc(-c2nc(-c3ccc(-c4ccccc4)cc3)nc(-c3ccc(-c4ccccc4)cc3)n2)c(O)c1)C(=O)OCCO]

(11)

A 500-mL flask was charged with 34 g of the precursor having formula (11), 130.5 g of propylene glycol monomethyl ether acetate, and 0.04 g of methoxyphenol. The contents were stirred and heated at 80° C. in a 4% oxygen/nitrogen atmosphere. Then, 21.8 g of 2-acryloyloxyethyl isocyanate (Karenz AOI, Showa Denko K.K.) and 0.04 g of dioctyltin oxide were added to the mixture, after which the reaction was run at 80° C. for 5 hours. The reaction mixture was cooled to room temperature and passed through a silica gel-packed column. The eluate was concentrated under reduced pressure, yielding 35.8 g of compound (S2) having formula (9).

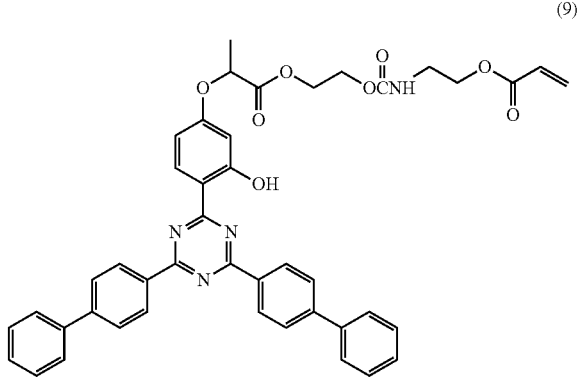

(9)

Reference Example 1

(Meth)Acrylic Group-Bearing Benzophenone Base UV Absorber

A methacrylic group-bearing benzophenone base UV absorber (RBP) was prepared by the method described in Example 2 of JP-A H06-88066.

Reference Example 2

Colloidal Silica Surface Treated with Acrylsilane

A mixture of 2.8 g of acryloyloxypropyltrimethoxysilane (KBM5103, Shin-Etsu Chemical Co., Ltd.), 95.6 g of methyl ethyl ketone silica sol (MEK-ST, Nissan Chemical Industries, Ltd., number average particle diameter 45 nm, silica concentration 30%) and 0.3 g of ion exchanged water was stirred at 80° C. for 3 hours. To the mixture was added 1.4 g of methyl orthoformate. The mixture was stirred and heated at the temperature for another hour, forming a dispersion of surface-treated silica particles. The dispersion was measured to have a solid concentration of 32%. The silica particles had an average particle diameter of 45 nm.

Preparation of Photo-Curable Coating Composition

Example 1

A photo-curable coating composition (C1) was prepared by blending 3.99 parts of compound (S1) obtained in Synthesis Example 1, 21.1 parts of dipentaerythritol penta- and hexa-acrylates (Aronix M403, Toagosei Co., Ltd.), 3.9 parts of 1,6-hexanediol diacrylate (HDDA, Daicel Cytec Co., Ltd.), 0.45 part of 1-hydroxycyclohexyl phenyl ketone (IRGACURE 184, BASF) as polymerization initiator, 0.45 part of 2,4,6-trimethylbenzoyldiphenylphosphine oxide (LUCILIN TPO, BASF) as polymerization initiator, 0.11 part of polyether-modified silicone (KP341, Shin-Etsu Chemical Co., Ltd.) as leveling agent, and 30 parts of propylene glycol monomethyl ether.

Examples 2 and 3 and Comparative Examples 1 to 4

Coating compositions (C2 and C3) of Examples 2 and 3 and coating compositions (R1 to R4) of Comparative Examples 1 to 4 were prepared in accordance with the formulation shown in Table 1 and the same procedure as in Example 1, using the compounds of Synthesis Examples 1 and 2 and Reference Examples 1 and 2 and commercial UV absorbers. A test piece was prepared by flow coating the coating composition on a surface of a polycarbonate sheet of 15 cm long×10 cm wide×5 mm thick (NF-2000, Mitsubishi Engineering-Plastics Corp.). The coating was air dried for 5 minutes and heated at 80° C. for 1 minute before it was cured by exposure to a high-pressure mercury lamp in an exposure dose of 600 mJ/cm$^2$ in a nitrogen atmosphere.

The coatings obtained in Examples and Comparative Examples were evaluated by the following methods, with the results shown in Table 1.

The abbreviations in Table 1 have the following meaning.
Component (1)
    A-M403: dipentaerythritol penta- and hexa-acrylates (Aronix M403, Toagosei Co., Ltd.)
    HDDA: 1,6-hexanediol diacrylate (HDDA, Daicel Cytec Co., Ltd.)

U-4HA: non-yellowing urethaneacrylate (U-4HA, Shin-Nakamura Chemical Co., Ltd.)

Component (2)
I184: 1-hydroxycyclohexyl phenyl ketone (IRGACURE 184, BASF)
L-TPO: 2,4,6-trimethylbenzoyldiphenylphosphine oxide (LUCILIN TPO, BASF)

Additive
KP341: polyether-modified silicone (KP341, Shin-Etsu Chemical Co., Ltd.)
Silica: dispersion of acrylsilane-surface-treated silica particles in Reference Example 2

Solvent
PGM: propylene glycol monomethyl ether

UV absorber
R93: 2-(2'-hydroxy-5'-methacryloxyethylphenyl)-2H-benzotriazole (RUVA-93, Otsuka Chemical Co., Ltd.)
RBP: (meth)acrylic group-bearing benzophenone base UV absorber in Reference Example 1
T405: 2-[4-[(2-hydroxy-3-(2'-ethyl)hexyl)oxy]-2-hydroxyphenyl]-4,6-bis(2,4-dimethylphenyl)-1,3,5-triazine (Tinuvin 405, BASF)

Evaluation Methods of Cured Film

Appearance of Coating

The coating was visually observed and rated according to the following criterion.
○: good
Δ: colored
x: unacceptable due to foreign matter, unevenness or whitening Mar Resistance Using a Taber abrader equipped with abrasive wheels CS-10F, the test piece was rotated under a load of 500 g according to ASTM 1044. After 500 cycles, haze (Hz) was measured. The difference (ΔHz) of haze before and after the test is reported as mar resistance.

Initial Adhesion

Adhesion was analyzed according to JIS K-5400, specifically by scribing the test piece with a razor along 6 longitudinal and 6 transverse lines at a spacing of 2 mm to define 25 square sections, tightly attaching a strip of Cellotape® (Nichiban Co., Ltd.) thereto, rapidly pulling back the adhesive tape at an angle of 90°, and counting the number (X) of coating sections kept unpeeled. The result is expressed as X/25.

Adhesion after Boiling

The test piece was immersed in boiling water for 2 hours, after which the adhesion test was carried out as above.

Weathering Test

Using an Eye Super UV Tester W-151 by Iwasaki Electric Co., Ltd., a weathering test was carried out. One cycle consisted of 5 hour holding at black panel temperature 63° C., relative humidity 50%, illuminance 50 mW/cm$^2$, and raining 10 seconds/hour, and 1 hour holding at black panel temperature 30° C. and relative humidity 95%. The weathering cycles were repeated for 100 hours, 200 hours, and 300 hours. After the test, the coating was observed with naked eyes and under a microscope (×250) and rated according to the following criterion.
○: good
Δ: some cracks or local peel
x: cracks or peel over entire coating surface

TABLE 1

|  |  | Example | | | Comparative Example | | | |
|---|---|---|---|---|---|---|---|---|
|  |  | 1 | 2 | 3 | 1 | 2 | 3 | 4 |
|  | Ingredient | C1 | C2 | C3 | R1 | R2 | R3 | R4 |
| Formulation (pbw) | | | | | | | | |
| Component (3) or UV absorber | S1 | 3.99 | | 5.32 | | | | |
| | S2 | | 3.99 | | | | | |
| | R93 | | | | | 3.99 | | |
| | RBP | | | | | | 3.99 | |
| | T405 | | | | | | | 3.99 |
| Component (1) | A-M403 | 21.1 | 21.1 | 10.0 | 21.1 | 21.1 | 21.1 | 21.1 |
| | HDDA | 3.9 | 3.9 | 3.9 | 3.9 | 3.9 | 3.9 | 3.9 |
| | U-4HA | | | 11.1 | | | | |
| Component (2) | I184 | 0.45 | 0.45 | 0.45 | 0.45 | 0.45 | 0.45 | 0.45 |
| | L-TPO | 0.45 | 0.45 | 0.45 | 0.45 | 0.45 | 0.45 | 0.45 |
| Additive | KP341 | 0.11 | 0.11 | 0.11 | 0.11 | 0.11 | 0.02 | 0.02 |
| | Silica | | | 2.0 | | | | |
| Solvent | PGM | 30 | 30 | 30 | 30 | 30 | 30 | 30 |
| Total | | 60 | 60 | 63 | 60 | 60 | 60 | 60 |
| Coating evaluation | | | | | | | | |
| Appearance | | ○ | ○ | ○ | ○ | x whitened | ○ | ○ |
| Initial Hz | | 0.43 | 0.39 | 0.55 | 0.28 | | 0.40 | 0.41 |
| Mar resistance | | 8.1 | 9.2 | 9.6 | 6.9 | | 9.3 | 16.3 |
| Initial adhesion | | 25 | 25 | 25 | 25 | | 25 | 25 |
| Adhesion after boiling | | 25 | 25 | 25 | 25 | | 25 | 10 |
| Weathering test | 100 h | ○ | ○ | ○ | x peeled | | ○ | ○ |
| | 200 h | ○ | ○ | ○ | | | ○ | Δ |
| | 300 h | ○ | ○ | ○ | | | x peeled | x peeled |

Although the films (C1 to C3) of Examples 1 to 3 exhibited a slight loss of mar resistance as compared with the UV absorber-free film (R1) of Comparative Example 1, they still retained a ΔHz value of less than 10 and exhibited improved weather resistance. The film (C3) of Example 3 maintained mar resistance equivalent, despite the increased amount of UV absorber, because surface-treated silica was supplemented. On the other hand, the film (R2) of Comparative Example 2 comprising a (meth)acrylic group-bearing benzotriazole base UV absorber other than component (3) became whitened because the UV absorber was not fully dissolved in the composition. The film (R3) of Comparative Example 3 comprising a benzophenone base UV absorber exhibited equivalent mar resistance to the films (C1) and (C2), but inferior weather resistance. The film (R4) of Comparative Example 4 comprising a (meth)acrylic group-free triazine base UV absorber exhibited poor mar resistance, adhesion, and weather resistance. This is probably because the UV absorber is not incorporated into the binder. The benefits of the photo-curable coating composition of the invention have been demonstrated.

Japanese Patent Application No. 2014-128136 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A coated article comprising a substrate which is coated with a photo-curable coating composition directly or via another layer,
   wherein the photo-curable coating composition comprises (1) a polyfunctional (meth)acrylic monomer, (2) a photopolymerization initiator, and (3) a hydroxyphenyltriazine base UV absorber having the general formula (1):

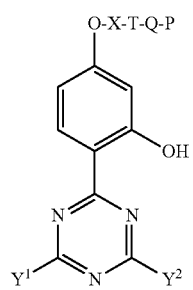

(1)

wherein $Y^1$ and $Y^2$ are each independently a substituent having the general formula (2):

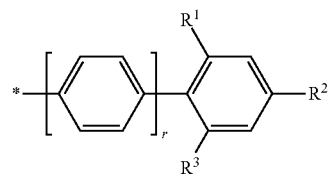

(2)

wherein * designates a bonding site, r is 0 or 1, $R^1$, $R^2$ and $R^3$ are each independently hydrogen, or hydroxyl, C1-C20 alkyl, C4-C12 cycloalkyl, C2-C20 alkenyl, C1-C20 alkoxy, C4-C12 cycloalkoxy, C2-C20 alkenyloxy, C7-C20 aralkyl, halogen, —C≡N, C1-C5 haloalkyl, —SO$_2$R', —SO$_3$H, —SO$_3$M wherein M is an alkali metal, —COOR', —CONHR', —CONR'R", —OCOOR', —OCOR', —OCONHR', (meth)acrylamino, (meth)acryloxy group, optionally substituted C6-C12 aryl or optionally substituted C3-C12 heteroaryl group, wherein R' and R" are independently hydrogen, C1-C20 alkyl, C4-C12 cycloalkyl, optionally substituted C6-C12 aryl or optionally substituted C3-C12 heteroaryl group, X is a divalent, straight or branched, saturated hydrocarbon residue which may be separated by at least one atom selected from oxygen, nitrogen, sulfur, and phosphorus, T is a urethane group: —O—(C=O)—NH—, Q is a divalent, straight or branched, saturated hydrocarbon residue which may be separated by at least one oxygen, and P is a (meth)acryloxy group.

2. The coated article of claim 1 wherein X has the general formula (3) or (4):

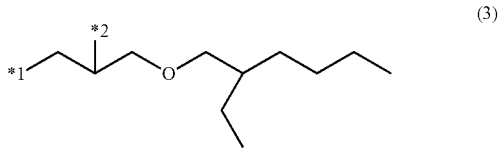

(3)

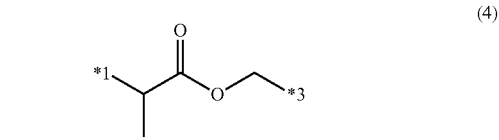

(4)

wherein *1 bonds to oxygen in formula (1), *2 bonds to T in formula (1), and *3 bonds to T in formula (1) directly or through a divalent, straight or branched, saturated hydrocarbon group which may be separated by at least one atom selected from oxygen, nitrogen, sulfur, and phosphorus, and Q has the general formula (5):

(5)

wherein *4 bonds to T in formula (1) and *5 bonds to P in formula (1).

3. The coated article of claim 2, wherein $R^1$, $R^2$ and $R^3$ in formula (1) are each independently hydrogen or methyl, X is formula (3), and Q is formula (5).

4. The coated article of claim 1, wherein the polyfunctional (meth)acrylic monomer is at least one monomer selected from the group consisting of dipentaerythritol penta(meth)acrylate, dipentaerythritol hexa(meth)acrylate, tris(2-(meth)acryloxyalkyl)isocyanurate, polyurethane poly(meth)acrylate having at least 5 (meth)acrylic groups in the molecule, and polyester poly(meth)acrylate having at least 5 (meth)acrylic groups in the molecule.

5. The coated article of claim 1, wherein the photo-curable coating composition further comprises colloidal silica surface treated with a (meth)acrylic functional alkoxysilane.

6. The coated article of claim 1, wherein the photo-curable coating composition further comprises at least one member selected from the group consisting of:
  (i) hindered amine photostabilizers,
  (ii) metal oxide fine particles other than colloidal silica surface treated with a (meth)acrylic functional alkoxysilane, and
  (iii) UV absorbers other than the hydroxyphenyltriazine base UV absorber having the general formula (1).

7. The coated article of claim 1 wherein the substrate is an organic resin or wood.

* * * * *